United States Patent [19]

Rendenbach-Mueller et al.

[11] Patent Number: 5,401,743
[45] Date of Patent: Mar. 28, 1995

[54] AMINOALKYL-SUBSTITUTED 2-AMINO-5-MERCAPTOTHIADIAZOLES THE PREPARATION AND USE THEREOF

[75] Inventors: Beatrice Rendenbach-Mueller, Waldsee; Hans-Juergen Teschendorf, Dudenhofen; Liliane Unger, Ludwigshafen, all of Germany

[73] Assignee: BASF Aktiengesellschaft, Ludwigshafen, Germany

[21] Appl. No.: 162,117

[22] PCT Filed: May 8, 1992

[86] PCT No.: PCT/EP92/01003
§ 371 Date: Dec. 13, 1993
§ 102(e) Date: Dec. 13, 1993

[87] PCT Pub. No.: WO92/22542
PCT Pub. Date: Dec. 23, 1992

[30] Foreign Application Priority Data
Jun. 15, 1991 [DE] Germany .................. 41 19 758.5

[51] Int. Cl.⁶ .................. C07D 285/135; C07D 417/12; A01K 31/41; A01K 31/435

[52] U.S. Cl. .................. 514/252; 514/326; 514/333; 514/363; 544/367; 546/209; 546/277; 548/141

[58] Field of Search .................. 548/141; 544/367; 546/209, 277; 514/252, 326, 333, 363

[56] References Cited

U.S. PATENT DOCUMENTS

4,074,049 2/1978 Begin et al. .................. 548/14

OTHER PUBLICATIONS

Chem. Abstr. JP 2 153 276 vol. 107, 1987—p. 791.

*Primary Examiner*—Robert Gerstl
*Attorney, Agent, or Firm*—Keil & Weinkauf

[57] ABSTRACT

Aminoalkyl-substituted 2-amino-5-mercapto-1,3,4-thiadiazole derivatives of the formula

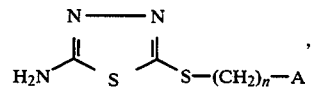

where A and n have the meanings stated in the description, and the preparation thereof are described. The compounds are suitable for controlling diseases.

4 Claims, No Drawings

AMINOALKYL-SUBSTITUTED 2-AMINO-5-MERCAPTOTHIADIAZOLES THE PREPARATION AND USE THEREOF

The present invention relates to aminoalkyl-substituted 2-amino-5-mercaptothiadiazoles, the preparation thereof and the use thereof for controlling diseases.

U.S. Pat. No. 4,074,049 describes aminoalkylthio-thiadiazoles which act as fungicides and inhibitors of platelet aggregation. JP 2 153 276 describes similar compounds which are used for treating liver disorders.

We have now found that aminoalkyl-substituted 2-amino-5-mercapto-1,3,4-thiadiazole derivatives of the formula I

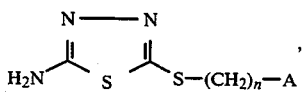

where
n is an integer from 2 to 6, and
A is

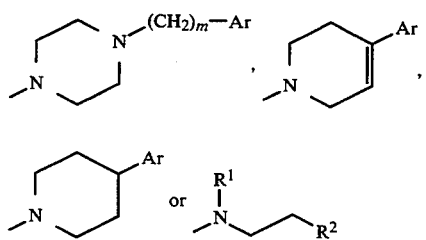

where Ar is phenyl which is unsubstituted or monosubstituted by $C_1$-$C_5$-alkyl, $C_1$-$C_5$-alkoxy, halogen, nitro, hydroxyl, trifluoromethyl or cyano, or is pyridyl, pyrimidinyl or thienyl, $R^1$ is hydrogen or $C_1$-$C_5$-alkyl, and $R^2$ is phenyl which is unsubstituted or monosubstituted by $C_1$-$C_5$-alkyl, $C_{2539}\gamma_1$-$C_5$-alkoxy, halogen, hydroxyl or trifluoromethyl, or is thienyl, and m is 0, 1 or 2,
and their salts with physiologically tolerated acids have interesting pharmacological properties.

In the formula I, A is preferably

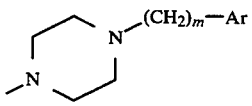

(m=0), Ar=phenyl, pyridyl, pyrimidinyl),

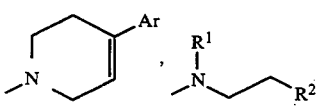

($R^1$-$C_1$-$C_4$-Alkyl, $R^2$-phenyl, thienyl)
and n is preferably 2 or 3.

The compounds of the formula I can be prepared by
a) reacting alkylamines of the formula II

X—(CH$_2$)$_n$—A    II, where n and A are as defined above, and X is a leaving group such as chlorine, bromine or $R^3SO_2O$—(where $R^3$ is lower alkyl or phenyl which is unsubstituted or substituted by $C_1$-$C_3$-alkyl or halogen), or a hydrohalic acid salt of these compounds, with 2-amino-5-mercapto-thiadiazole or an alkali metal salt of this compound, or
b) reacting a thiadiazole of the formula III

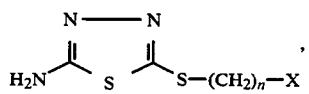

where n has the abovementioned meanings, and X is as defined in a), with an amine of the formula IV

H—A    IV, where A has the stated meanings, and converting the resulting compounds where appropriate into their salts with physiologically tolerated acids.

The reactions in process a) preferably take place in a solvent at from room temperature to the boiling point of the solvent, where appropriate in the presence of an acid acceptor. Examples of solvents which can be used are aliphatic alcohols, dimethylformamide, dimethoxyethane, tetrahydrofuran, toluene, xylene or a ketone such as acetone or butanone, and suitable acid acceptors are inorganic bases such as sodium or potassium carbonate or organic bases such as triethylamine or pyridine. The latter can also act as solvent. The crude product is isolated in a conventional way, eg. by filtration, removal of the solvent by distillation, or extraction from the reaction mixture. The resulting compound is purified in a conventional way, for example by recrystallisation from a solvent, chromatography or conversion into an acid addition compound.

The alkylamines of the formula II used as starting materials are known from the literature or can be obtained in a conventional way by alkylation of the amines of the formula IV with ω-X-substituted $C_2$-$C_6$-alkyl halides.

The reactions in process b) take place in the melt, if required also in the presence of a solvent, eg. ethyl acetate, tetrahydrofuran, dimethylformamide, dimethoxyethane, toluene or xylene, at from room temperature to the boiling point of the solvent, preferably in the presence of a base such as sodium methylate, sodium ethylate, sodium hydride, sodium carbonate, potassium carbonate, or of an amine, eg. pyridine. It is also possible where appropriate for the amine component IV in excess to act as reagent, base and solvent.

The resulting compounds according to the invention are, where appropriate, converted into their addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid and benzoic acid. Others are to be found in Fortschritte der Arzneimittelforschung, Vol. 10, pp. 224 et seq., Birkh‚uml/a/ user Verlag, Basel and Stuttgart, 1966.

The acid addition salts are usually obtained in a conventional way by mixing the free base or solutions thereof with the appropriate acid or solutions thereof in an organic solvent, for example a lower alcohol such as methanol, ethanol or propanol, a halohydrocarbon such as methylene chloride, an ether such as methyl t-butyl ether or diisopropyl ether, a ketone such as acetone or butanone or an ester such as ethyl acetate. It is also possible to use mixtures of the said solvents to improve crystallization. In addition, pharmaceutically acceptable aqueous solutions of acid addition compounds of the compounds I according to the invention can be prepared by dissolving the free bases in an aqueous acid solution.

The compounds according to the invention are suitable for controlling diseases, especially for treating disorders of the central nervous system (eg. parkinsonism, schizophrenia) and high blood pressure. They have, in particular, valuable properties as dopamine receptors, in some cases with selectivity for presynaptic dopamine receptors, or as dopamine antagonists. The compounds of the formula I show affinity for the dopamine receptor in receptor binding assays; they inhibit motility in mice (measured in cages with a photoelectric beam) and influence the pivoting behavior of rats with unilateral 6-hydroxydopamine lesions of the substantia nigra (Brain Research 24, (1970) 485–493).

The effects of the novel compounds can be shown in the receptor binding assay as follows:

Striata from rats (Sprague Dawley, Charles River) were homogenized immediately after removal in 0.32M sucrose solution (0° C.). The homogenate was filtered through gauze, the filtrate was centrifuged at 1000 xg (5 min at 4° C.) and the resulting supernatant was centrifuged at 40000 xg (4° C., 10 min). The residue (membranes) was taken up in incubation buffer (50 mM tris-HCl, 1 mM $MgCl_2$ and 0.1% ascorbic acid, pH 7.4) and incubated at 37° C. for 20 min. The residue was subsequently washed 2× with incubation buffer by resuspension and recentrifugation. The membranes were frozen in portions in liquid nitrogen.

The assay mixtures (1 ml) were composed of membranes (380 μg of protein), 1 nM $^3$H-ADTN (NEN, Dreieich Germany, specific radioactivity 1.4 TBq/mmol) and 0.1 μM SCH 23390 (total binding) or a) with the addition of 50 nM spiperone (non-specific binding) or b) with test substance. The mixtures were prepared in triplicate.

After the incubation (40 min at 25° C.) the mixtures were filtered through glass fiber filters (Whatman GF/B) and briefly washed with ice-cold washing buffer (Tris-HCl, pH 7.4). The radioactivity retained on the filters was determined by liquid scintillation counting. The non-specific binding comprised about 40–50% of the total binding.

The evaluation of the competition plots and the determination of the dissociation constant took place by iterative non-linear regression analysis based on the "ligand" program (Muson and Rodbard: Anal. Biochem. 107 (1980) 220).

Affinity of the test substances for the dopamine $D_2$ receptor

| Example | Ki (nM) |
| --- | --- |
| 1 | 125 |
| 3 | 12 |
| 4 | 6 |
| 8 | 45 |
| 9 | 45 |
| 11 | 15 |
| 14 | 36 |

The compounds according to the invention can be administered orally or parenterally (subcutaneously, intravenously, intramuscularly, intraperitoneally) in a conventional way. Administration can also take place through the nasopharyngeal space using vapors or sprays.

The dosage depends on the age, condition and weight of the patient and on the mode of administration. The dose of active substance is, as a rule, about 10–500 mg per patient and day on oral administration and about 1–50 mg per patient and day on parenteral administration.

The novel compounds can be used in the conventional solid or liquid pharmaceutical forms, eg. as uncoated or (film-coated) coated tablets, capsules, powders, granules, suppositories, solutions or sprays. These are produced in a conventional way. The active substances can be processed with conventional pharmaceutical aids such as tablet binders, fillers, preservatives, tablet disintegrants, flow regulators, plasticizers, wetting agents, dispersants, emulsifiers, solvents, retarding agents, antioxidants and/or propellant gases (cf. H. Sucker et al.: Pharmazeutische Technologie, Thieme-Verlag, Stuttgart, 1978). The pharmaceutical forms obtained in this way normally contain the active substance in an amount of from 1 to 99% by weight.

The following examples illustrate the invention:

EXAMPLE 1

2-Amino-5-[3-(4-fluorophenylpiperazinyl)propylthio]-1,3,4-thiadiazole dihydrochloride 4.0 g of 2-amino-5-mercapto-1,3,4-thiadiazole and 11 g of potassium carbonate were introduced into 50 ml of dimethylformamide and, after addition of 7.6 g of 1-(3-chloropropyl)-4-(4-fluorophenyl)piperazine, the mixture was heated at 100° C. for 30 min, then cooled and poured into ice-water. The precipitated solid was filtered off with suction and purified by crystallisation from ethyl acetate and ethanol. The crystals were dissolved in methanol, ethereal HCl was added, and the dihydrochloride was precipitated by adding methyl t-butyl ether. The solid was filtered off with suction and dried under reduced pressure.

Yield: 3.8 g (30%),
melting point: 209°–211°

EXAMPLE 2

2-Amino-5-[2-(2-phenylethyl-n-propylamino)ethylthio]-1,3,4-thiadiazole dihydrochloride 4 g of 2-amino-5-mercapto-1,3,4-thiadiazole, 2.5 g of potassium carbonate and 7.0 g of 2-chloroethyl-(n-propyl)phenethylamine in 10 ml of dimethylformamide were stirred at 100° C. for 30 min. The mixture was then cooled and poured into ice-water, and the precipitated brown solid was filtered off with suction and partitioned in methyl t-butyl ether/water. The organic phase was separated off, washed with water and concentrated. The residue was taken up in 2N HCl and extracted with methylene chloride. The aqueous phase was adjusted to pH 7 with 2N NaOH, the precipitated white solid was filtered off with suction and suspended in i-propanol, and ethereal HCl was added. The white solid which was precipated by addition of methyl t-butyl ether was filtered off with suction and dried under reduced pressure.

Yield: 5.7 g (47%)
Melting point: 100°–104° C.

The following were prepared as in Example 1 or 2:

EXAMPLE 3

2-Amino-5-[2-(4-phenyl-1,2,3,6-tetrahydropyridyl)-ethylthio]-1,3,4-thiadiazole dihydrochloride Yield: 29% Melting point: 205°–206° C.

EXAMPLE 4

2-Amino-5-[3-(4-phenyl-1,2,3,6-tetrahydropyridyl)-propylthio]-1,3,4-thiadiazole hydrochloride Yield: 45%
Melting point: 192° C.

EXAMPLE 5

2-Amino-5-[2-(4-phenylpiperazinyl)ethylthio]-1,3,4-thiadiazole hydrochloride

Yield: 27%
Melting point: 123°–124° C.

EXAMPLE 6

2-Amino-5-[2-(4-pyrid-2-ylpiperazinyl)ethylthio]-1,3,4-thiadiazole dihydrochloride Yield: 46%
Melting point: 164° C.

EXAMPLE 7

2-Amino-5-[2-(4-pyrimidin-2-ylpiperazinyl)ethylthio]-1,3,4-thiadiazole dihydrochloride Yield: 69%
Melting point: 208° C.

EXAMPLE 8

2-Amino-5-[2-(4-phenylpiperidinyl)ethylthio]-1,3,4-thiadiazole hydrochloride

Yield: 62%
Melting point: 180°–181° C.

EXAMPLE 9

2-Amino-5-[3-(2-phenylethyl-n-propylamino)propylthio]-1,3,4-thiadiazole tartrate Yield: 32%
Melting point: 145°–146° C.

EXAMPLE 10

2-Amino-5-[2-(4-(2-nitrophenyl)piperazinyl)ethylthio]-1,3,4-thiadiazole hydrochloride Yield: 36%
Melting point: 210°–211° C.

EXAMPLE 11

2-Amino-5-[2-(4-(2-ethoxyphenyl)piperazinyl)ethylthio]-1,3,4-thiadiazole hydrochloride Yield: 54%
Melting point: 210° C.

EXAMPLE 12

2-Amino-5-[2-(4-(4-chlorophenyl)piperazinyl)ethylthio]-1,3,4-thiadiazole hydrochloride Yield: 60%
Melting point: 212°–213° C.

EXAMPLE 13

2-Amino-5-[3-(4-(3-methoxyphenyl)piperazinyl)propylthio]-1,3,4-thiadiazole hydrochloride Yield: 58%
melting point: 212° C.

EXAMPLE 14

2-Amino-5-[3-(4-(3-methylphenyl)piperazinyl)propylthio]-1,3,4-thiadiazole hydrochloride Yield: 54%
Melting point: 225°–226° C.

EXAMPLE 15

2-Amino-5-[3-(4-(3-chlorophenyl)piperazinyl)propylthio]-1,3,4-thiadiazole hydrochloride Yield: 55%
Melting point: 187° C.

EXAMPLE 16

2-Amino-5-[3-(4-phenethylpiperazinyl)propylthio]-1,3,4-thiadiazole hydrochloride Yield: 50%
Melting point: 194°–195° C.

EXAMPLE 17

2-Amino-5-[2-(4-(2-methoxyphenyl)piperazinyl)ethylthio]-1,3,4-thiadiazole hydrochloride Yield: 52%
Melting point: 182°–183° C.

EXAMPLE 18

2-Amino-5-[2-(4-(2-cyanophenyl)piperazinyl)ethylthio]-1,3,4-thiadiazole hydrochloride Yield: 37%
Melting point: 211°–212° C.

EXAMPLE 19

2-Amino-5-[2-(4-(3-trifluoromethylphenyl)piperazinyl)ethylthio]-1,3,4-thiadiazole hydrochloride Yield: 28%
Melting point: 145°–146° C.

EXAMPLES OF PHARMACEUTICAL FORMS

A) Tablets of the following composition are made in a tableting machine in a conventional way.

40 mg of substance of Example 1
120 mg of corn starch
13.5 mg of gelatin
45 mg of lactose
2.25 mg of Aerosil ® (chemically pure silica in sub-microscopically fine distribution)
6.75 mg of potato starch (as 6% paste)

B) 20 mg of substance of Example 4
60 mg of core composition
60 mg of coating composition The core composition comprises 9 parts of corn starch, 3 parts of lactose and 1 part of 60:40-vinylpyrrolidone/vinyl acetate copolymer. The coating composition comprises 5-parts of sucrose, 2 parts of corn starch, 2 parts of calcium carbonate and 1 part of talc. The coated tablets produced in this way are subsequently provided with an enteric coating.

C) 10 g of substance of Example 2 are dissolved in 5000 ml of water with the addition of NaCl and adjusted to pH 6.0 with 0.1 N NaOH to produce a solution isotonic with blood. 1 ml portions of this solution are introduced into ampoules and sterilized.

We claim:

1. An aminoalkyl-substituted 2-amino-5-mercapto-1,3,4-thiadiazole derivative of the formula I

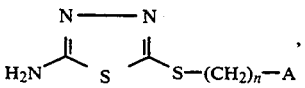

where
n is an integer from 2 to 6, and
A is

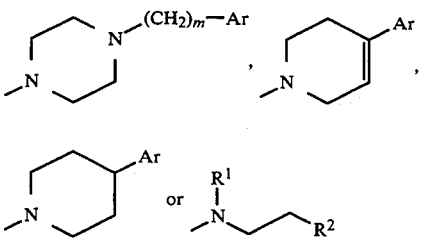

where Ar is phenyl which is unsubstituted or monosubstituted by $C_1$–$C_5$-alkyl, $C_1$–$C_5$-alkoxy, halogen, nitro, hydroxyl, trifluoromethyl or cyano, or is pyridyl, pyrimidinyl or thienyl, $R^1$ is hydrogen or $C_1$–$C_5$-alkyl, and $R^2$ is phenyl which is unsubstituted or monosubstituted by $C_1$–$C_5$-alkyl, $C_1$–$C_5$-alkoxy, halogen, hydroxyl or trifluoromethyl, or is thienyl, and m is 0, 1 or 2, and its salts with physiologically tolerated acids.

2. The aminoalkyl-substituted 2-amino-5-mercapto-1,3,4-thiadiazole derivatives of formula I, as defined in claim 1, wherein A is

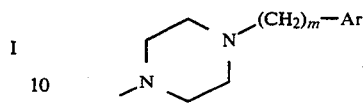

where Ar is phenyl, pyridyl or pyrimidinyl, and m is 0;

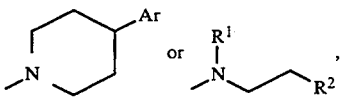

where $R^1$ is $C_{1-4}$ alkyl and $R^2$ is phenyl or thienyl; and n is 2 or 3.

3. A method for controlling high blood pressure, Parkinson's disease and schizophrenia, which comprises administering to a patient in need thereof an effective amount of the aminoalkyl-substituted 2-amino-5-mercapto-1,3,4-thiadiazole derivative of the formula I as defined in claim 1.

4. A pharmaceutical composition for treating high blood pressure, Parkinson's disease and schizophrenia, which comprises the aminoalkyl-substituted 2-amino-5-mercapto-1,3,4-thiadiazole derivative of the formula I as defined in claim 1 and pharmaceutically acceptable carriers and/or additives.

* * * * *